US009063039B1

(12) United States Patent
Tsantinis et al.

(10) Patent No.: US 9,063,039 B1
(45) Date of Patent: Jun. 23, 2015

(54) SOFT BODY ARMOR DURABILITY TESTER

(71) Applicant: The United States of America as Represented by the Secretary of the Army, Washington, DC (US)

(72) Inventors: Nicholas Tsantinis, Auburn, MA (US); Richard P. Gallimore, Milford, MA (US); Gary N. Proulx, Harrisville, RI (US); Jason C. Parker, Grafton, MA (US)

(73) Assignee: The United States of America as by the Secretary of the Army, Washington, DC (US)

( * ) Notice: Subject to any disclaimer, the term of this patent is extended or adjusted under 35 U.S.C. 154(b) by 0 days.

(21) Appl. No.: 14/030,285

(22) Filed: Sep. 18, 2013

Related U.S. Application Data

(60) Provisional application No. 61/702,766, filed on Sep. 19, 2012.

(51) Int. Cl.
*G01N 3/22* (2006.01)
*G01L 5/24* (2006.01)
*F41H 5/08* (2006.01)
*F41H 1/02* (2006.01)

(52) U.S. Cl.
CPC .. *G01N 3/22* (2013.01); *F41H 1/02* (2013.01); *G01L 5/24* (2013.01)

(58) Field of Classification Search
CPC ..................................... F41H 1/02; G01L 5/24
USPC ..................................... 73/847, 866; 89/36.05
See application file for complete search history.

(56) References Cited

U.S. PATENT DOCUMENTS

| | | | | |
|---|---|---|---|---|
| 6,826,963 | B2 * | 12/2004 | Liu et al. | 73/798 |
| 6,860,156 | B1 * | 3/2005 | Cavallaro et al. | 73/819 |
| 7,204,160 | B1 * | 4/2007 | Sadegh et al. | 73/862.041 |
| 7,895,899 | B2 * | 3/2011 | Kelly et al. | 73/760 |
| 8,082,802 | B1 * | 12/2011 | Sadegh et al. | 73/856 |
| 8,262,383 | B2 * | 9/2012 | Harris et al. | 425/391 |
| 8,302,488 | B2 * | 11/2012 | Hsu et al. | 73/856 |
| 8,453,520 | B2 * | 6/2013 | Huang et al. | 73/862.191 |
| 2012/0167662 | A1 | 7/2012 | Ardiff | |
| 2013/0249157 | A1 * | 9/2013 | Endo et al. | 269/56 |

FOREIGN PATENT DOCUMENTS

WO    2009055297 A3    4/2009

* cited by examiner

*Primary Examiner* — Lisa Caputo
*Assistant Examiner* — Jonathan Dunlap
(74) *Attorney, Agent, or Firm* — Roger C. Phillips

(57) ABSTRACT

An assembly for testing a durability of a soft body armor system includes a top mounting assembly, a bottom mounting assembly, the soft body armor system being fixedly disposed between the top mounting assembly and the bottom mounting assembly, a rotary actuator coupled to the top mounting assembly, the rotary actuator configured to rotate the top mounting assembly in a range of approximately +90 degrees to and including −90 degrees, a linear bearing on each end of the bottom mounting assembly, and a bearing rod on which each linear bearing is configured to ride. A rotation of the top mounting assembly induces torsional, axial and bending forces substantially simultaneously on the soft body armor system.

17 Claims, 9 Drawing Sheets

SOFT BODY ARMOR DURABILITY TESTER

CROSS REFERENCE TO RELATED APPLICATION

This application claims benefit of U.S. Provisional Application No. 61/702,766, filed Sep. 19, 2012, entitled "Soft Body Armor Durability Tester".

STATEMENT OF GOVERNMENT INTEREST

The invention described herein may be manufactured and used by or for the U.S. Government for governmental purposes without the payment of any royalties thereon or therefor.

FIELD

The aspects of the present disclosure relate generally to the field of body armor, and in particular to durability testing of soft body armor.

BACKGROUND

Soft body armor durability entails many parameters and can be broadly described as the armor system's ability to withstand or resist wear from axial, torsional and bending motions, as well laundering, temperature and humidity exposure, POL and salt water exposure and non-penetrating blunt impact resistance.

The question of how long soft body armor will last is a frequent question of Army logisticians and law enforcement officials. Unfortunately, no definitive answer can be given to this question regarding service life, which encompasses many variables such as wear (including bending, twisting, and folding), care (including launderability, handling, and storage), and temperature/humidity exposure, etc. Every piece of body armor has a service life and will eventually have to be replaced.

Currently, the only method to quantitatively evaluate body armor performance is destructive ballistic testing. Age alone does not cause the body armor's ballistic resistance to deteriorate (shelf life). The care and maintenance of a garment (or the lack thereof) have been shown to have a greater impact to service life of body armor than shelf life. As of today there is no way to determine the service life of soft body armor. Having the ability to do so could reduce life-cycle costs associated with sustainment and re-issuance. More importantly, it could be used to determine if a soft body armor design can maintain its ballistic integrity for some expected level of use/time. Therefore, the need exists to identify relevant variables and meaningful methods of measuring the approximate service life of body armor systems based on actual wear and care (not just on shelf life alone).

Current test methods for abrasion resistance and durability of textile-based and film systems include ASTM (American Society for Testing and Materials) test methods. These methods typically involve mechanical oscillations to cause abrasion damage to a fabric sample. Generally, the approaches use a series of rollers and bars to apply stresses onto the test material. However, even methods that provide more complex motion mainly focus on testing one layer of fabric at a time, and not a system-level test of a full body armor system. Additionally, these types of testing systems only impart abrasion on the test material and do not focus on durability of the test material in an end user situation. It would be advantageous to accommodate a full body armor system in a durability test.

U.S. Pat. No. 8,225,638 (Honeywell) describes a system for testing the durability and wear resistance of soft armor. Honeywell relies on a reciprocating drive that forces the textile system back and forth along its length. The flexible fabrics are turned as it passes through the rollers. However, the use of rollers may not approximate the forces and stresses experienced in the use of ballistic resistant fabric and composite articles. These can include forces and stresses resulting from actions such as squatting (compression), bending (flexion/extension) and twisting (torsion). It would be advantageous to have a test apparatus capable of subjecting a multi-layered soft armor system to each of the forces and stresses that are typically experienced as a result of basic human motion that would be experienced during end-item use.

Accordingly, it would be desirable to provide a soft body armor durability test system and method that addresses at least some of the problems identified above.

BRIEF DESCRIPTION OF THE DISCLOSED EMBODIMENTS

As described herein, the exemplary embodiments overcome one or more of the above or other disadvantages known in the art.

One aspect of the exemplary embodiments relates to an assembly for testing the durability of a soft body armor system. In one embodiment, the system includes a top mounting assembly, a bottom mounting assembly, the soft body armor system being fixedly disposed between the top mounting assembly and the bottom mounting assembly, a rotary actuator coupled to the top mounting assembly, the rotary actuator configured to rotate the top mounting assembly in a range of approximately +90 degrees to and including −90 degrees, a linear bearing on each end of the bottom mounting assembly, and a bearing rod on which each linear bearing is configured to ride. A rotation of the top mounting assembly induces torsional, axial and bending forces substantially simultaneously on the soft body armor system.

Another aspect of the disclosed embodiments is directed to a method for durability testing of a soft body armor system. In one embodiment, the method includes positioning a ballistic shoot pack between a top mount assembly and a bottom mount assembly, the top mount assembly being configured to rotate about a vertical axis; rotating the top mount assembly to apply a torsional force to the ballistic shoot pack, the bottom mount assembly remaining stationary about the vertical axis.

Another aspect of the exemplary embodiments relates to a shoot pack durability test assembly. In one embodiment, the shoot pack test assembly includes a chassis; a set of bearing rods fixedly attached to the chassis; a bottom mount assembly having a first end and a second end; a linear bearing coupled to the first end and the second end of the bottom mount assembly and configured to ride on a respective bearing rod; a rotatory actuator coupled to the chassis; a top mount assembly coupled to the rotary actuator, the rotary actuator configured to rotate the top mount assembly in a range of between approximately +90 degrees to and including −90 degrees about a vertical axis between the bottom mount assembly and the top mount assembly; and a shoot pack disposed between the bottom mount assembly and the top mount assembly.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the present disclosure, and together with the general description given above and the detailed description given below, serve to explain the principles of the present disclosure. As shown throughout the drawings, like reference numerals designate like or corresponding parts.

DETAILED DESCRIPTION OF THE EXEMPLARY EMBODIMENTS OF THE DISCLOSURE

Figure 1:
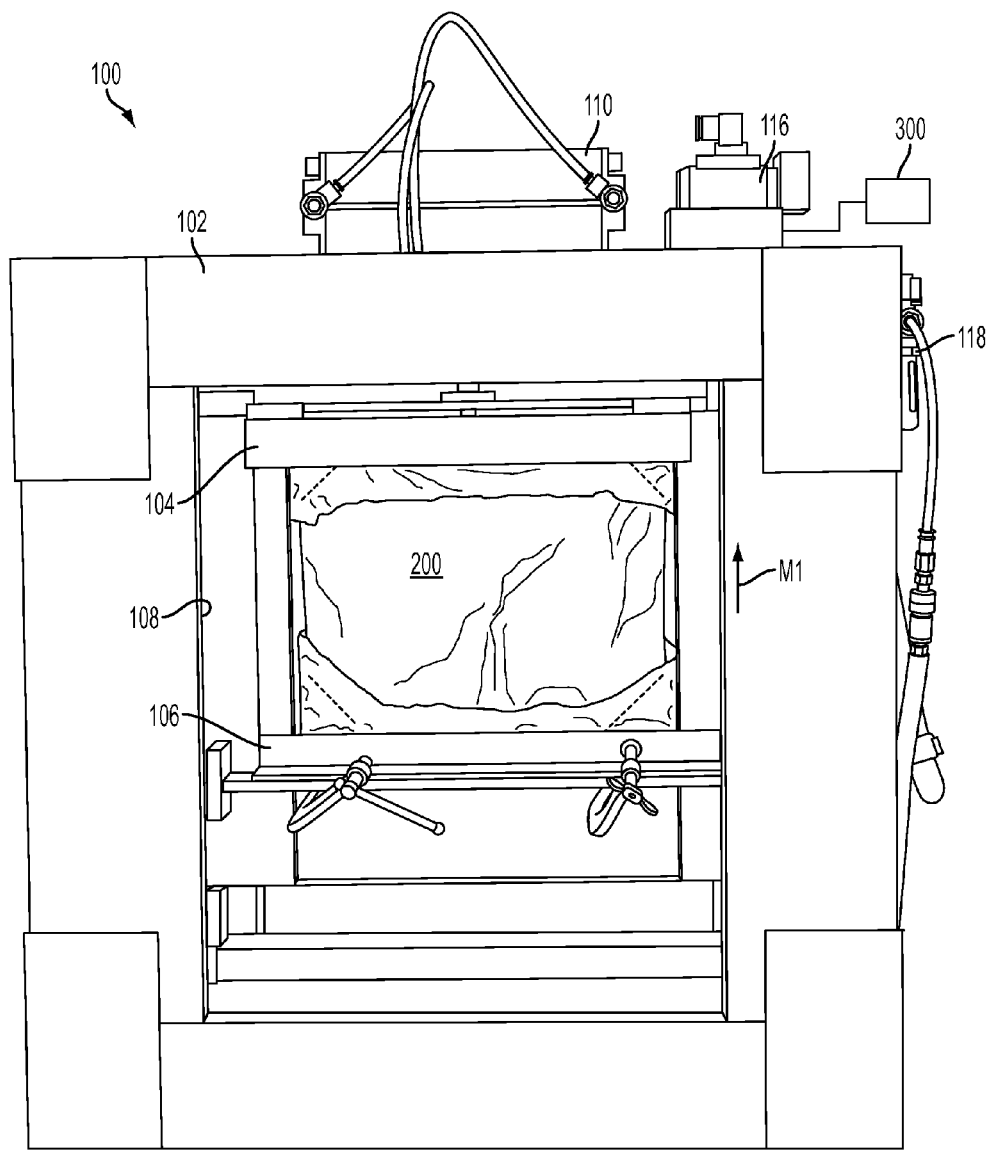
FIG. 1 illustrates a front view of one embodiment of a soft body armor test system incorporating aspects of the present disclosure.

Referring to FIG. 1, one embodiment of a soft body armor durability testing system incorporating aspects of the present disclosure is generally designated by reference numeral 100. The aspects of the disclosed embodiments are directed to a soft body armor durability testing system that is configured to apply a combination of axial, torsional and flexsion/extension forces to a ballistic shoot pack. A ballistic shoot pack, or shoot pack, as the term is used herein, will generally be understood to apply to an approximately 15 inch by 15 inch representation of a soft body armor component that includes ballistic filler(s), carrier fabric(s) and stitching to combine the two, where the mass per unit area (areal density) of the shoot pack is equal to its end-item counterpart. The shoot pack can be constructed of fabric based or composite based body armor systems. The application of three forces, in some cases in a substantially simultaneous fashion, generally simulates human motion to condition body armor via a simulated use condition. The body armor configuration which will be commonly tested with the system 100 is the soft body armor shoot pack, although in alternate embodiments, any suitable test object can be utilized.

As shown in FIG. 1, the soft body armor test system 100 generally includes a chassis 102, a top mounting assembly 104 and a bottom mounting assembly 106. A ballistic shoot pack 200 is movably and removably retained between the top mounting assembly 104 and the bottom mounting assembly 106, as will be further described herein. The bottom mounting assembly 106 floats or moves in a vertical fashion on linear bearings coupled or mounted to bearing rods 108. The top mounting assembly 104 is coupled to an actuator 110. In one embodiment, the actuator 110 is a rotary actuator. The top mounting assembly 104 is configured to rotate approximately 180 degrees relative to a vertical axis.

Figure 2:
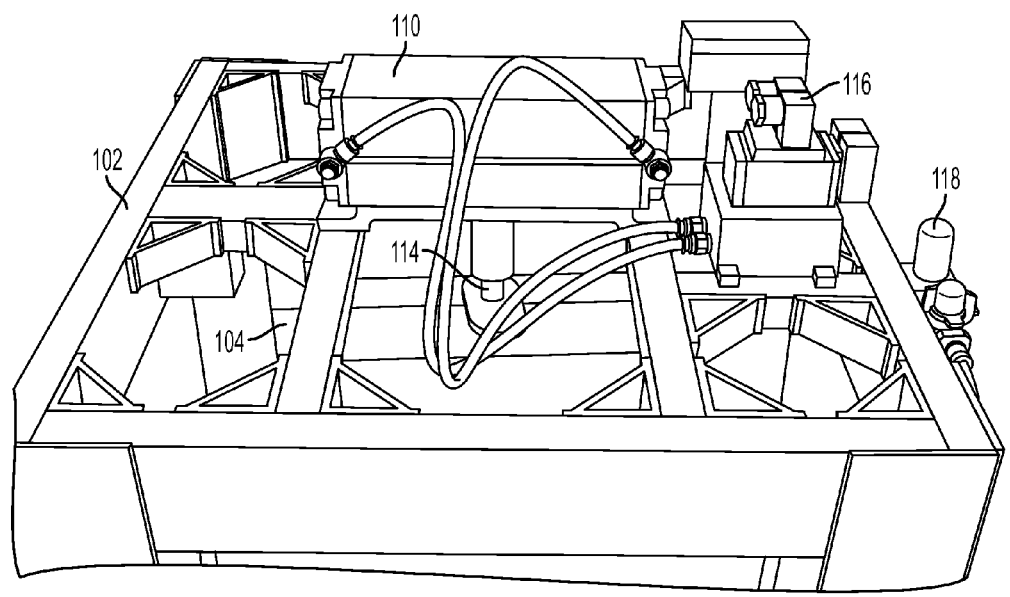
FIG. 2 illustrates a perspective top view of one embodiment of a soft body armor test system incorporating aspects of the present disclosure.

Referring to FIG. 2, which illustrates a top view of the system 100, in one embodiment, the system 100 can include one or more manifolds with attached solenoid valve(s) 116 that can be used to control the flow of air to the actuator 110. In the embodiment shown in FIG. 2, there are two single position solenoid valves 116 (ON or OFF). In alternate embodiments, any suitable solenoid position valve can be used. A regulator-air dryer 118 can be used to process the air flowing to the solenoid valves 116. In this embodiment, the actuator 110 is a pneumatic actuator. In alternate embodiments, the actuator 110 can comprise any suitable actuator, other than including a pneumatic actuator. For example, the actuator 110 can comprise an electrically operated actuator. In this example, the actuator 110 is coupled to the shaft coupler 114, which is in turn coupled to the top mounting assembly 106.

In one embodiment, the shoot pack 200 is preloaded in tension by the weight of the bottom mounting assembly 106, which may also be referred to as a clamping assembly. When the rotary actuator 110 is energized, the rotary actuator 110 imposes an immediate torsional force on the shoot pack 200. This torsional force causes a reduction in height of the shoot pack 200. Since the top section 202 of the shoot pack 200 is fixed at the actuator 110, generally by the top mounting assembly or clamping assembly 104, this causes the bottom section 204 of the shoot pack 200 to rise along the bearing rods 108, generally indicated by the arrow M1 in FIG. 1. This rise induces compressive stresses on the shoot pack 200 and causes it to undergo bending as the bottom portion 204 of the shoot pack 200 rises.

In one embodiment, the actuator 110 is configured to cycle between approximately -90 degrees and +90 degrees. This cycling is configured to impose cyclical rotational motion of approximately 180 degrees, in both clockwise and counter clockwise directions, on the shoot pack 200.

Figure 3:
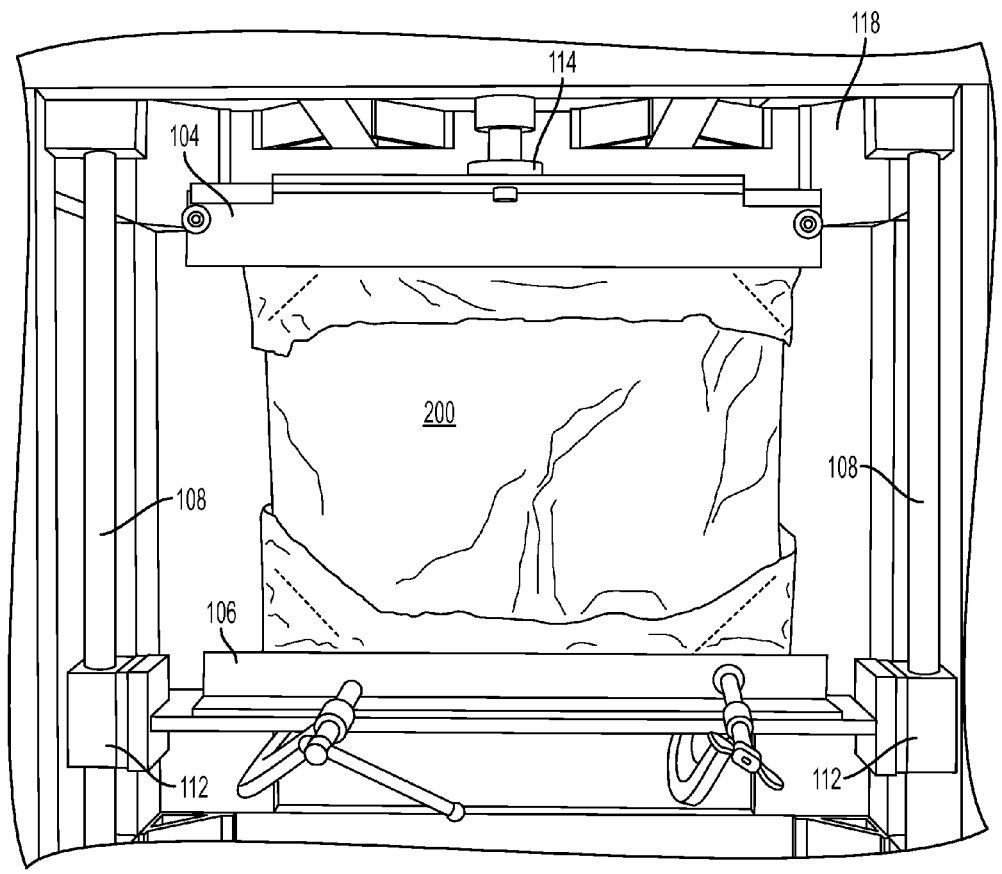
FIG. 3 illustrates a front view of one embodiment of a soft body armor test system incorporating aspects of the present disclosure, with a shoot pack in a starting position.

FIG. 3 illustrates one embodiment of the system 100 in the starting position. In this example, the shoot pack 200 is disposed between the top mounting assembly 104 and the bottom mounting assembly 106. The pillow block linear bearings 112 of the bottom mounting assembly are configured to ride upon the bearing rods 108. The shaft coupler 114 couples the top mounting assembly 104 to the actuator 110.

Figure 4:
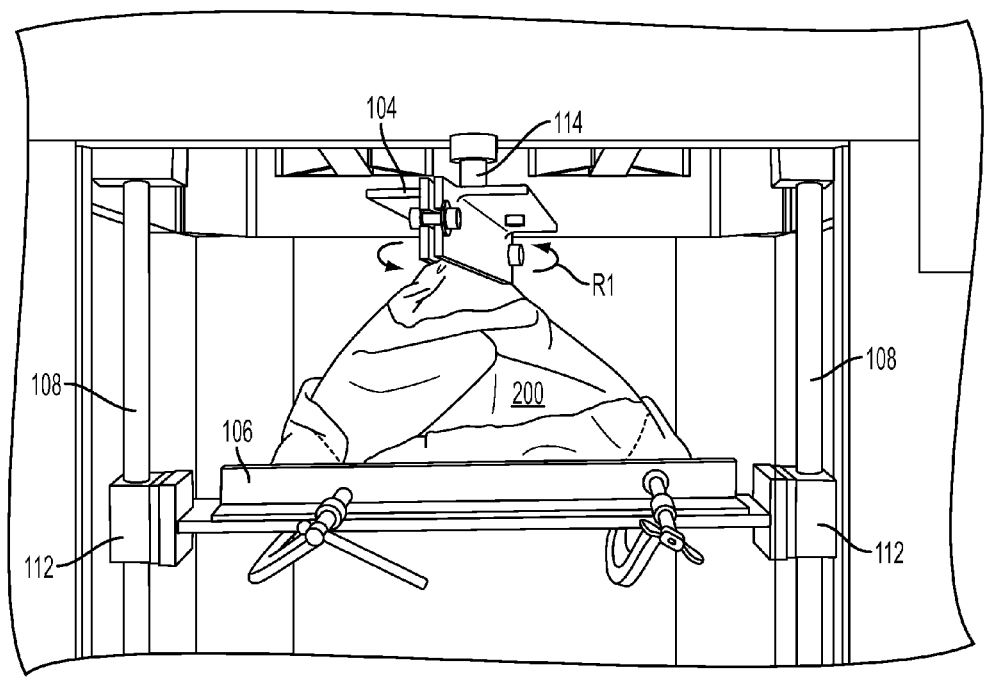
FIG. 4 a front view of one embodiment of a soft body armor test system incorporating aspects of the present disclosure, with a shoot pack in an actuated position.

FIG. 4 illustrates one embodiment of the device 100 in an actuated position. In this embodiment, the actuator 110 has caused the top mounting assembly 104 to rotate in a counter-clockwise direction (when viewed from the top of the system 100), as is generally indicated by arrow R1. The rotation of the top mounting assembly 104 imposes a torsional force on the shoot pack 200. This rotation also causes a reduction in height of the shoot pack 200, as the bottom mounting assembly 106 moves upward, carried by the linear bearings 112 on the bearing rods 108. The weight of the bottom mounting assembly 106 resists the movement of the shoot pack 200.

Figure 5:
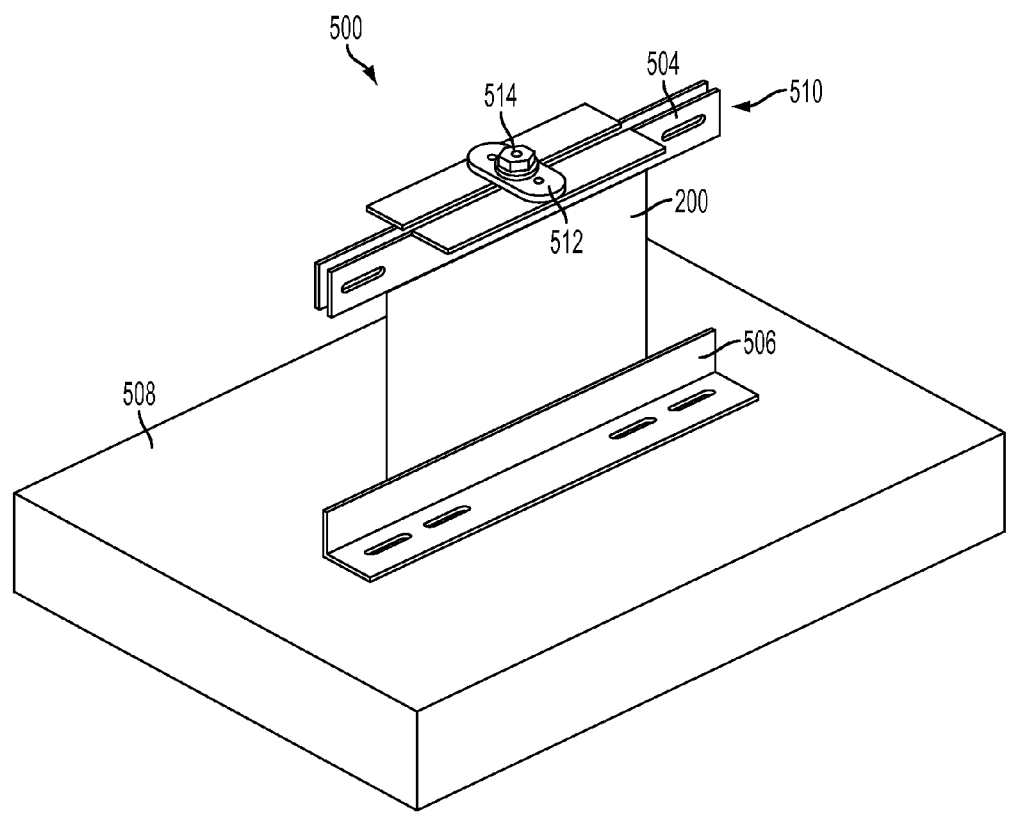
FIG. 5 illustrates a perspective view of one embodiment of a soft body armor test system incorporating aspects of the present disclosure.

FIG. 5 illustrates one embodiment of a soft body armor durability test system 500 incorporating aspects of the present disclosure. In this example, the testing system 500 includes a top mounting assembly 504 and a bottom mounting assembly 506, also referred to as clamping devices. The shoot pack 200 is disposed between the top mounting assembly 504 and bottom mounting assembly 506. In this example, the bottom mounting assembly 506 is coupled to a base member 508. Alternatively, the bottom mounting assembly 506 can be configured to float, such as is described with respect to FIG. 1.

In the embodiment of FIG. 5, the top mounting assembly 504 comprises an angle iron assembly 510. The top portion 202 of the shoot pack 200 is clamped in-between the angle iron assembly 510. In one embodiment, "C" style clamps, toggle clamps or nuts and bolts can be used to hold the shoot pack 200 in place in-between the angle iron assembly 510. In alternate embodiments, any suitable mechanism can be used to secure the top portion 202 of the shoot pack 200 to the angle iron assembly 510. In the example of FIG. 5, a top clamp assembly 512 is used to couple the angle iron assembly 510 together, thereby securing the top portion 202 of the shoot pack 200 in-between the angle iron assembly 510. In alternate embodiments, any suitable device can be used to couple the angle iron assembly together, such as for example toggle clamps.

In one embodiment, a bolt 514 is coupled to an approximate center top portion of the angle iron assembly 510, as is shown in FIG. 5 by rigidly affixing it to the top clamp assembly 512. In the embodiment shown in FIG. 5, the bolt 514 is welded to the clamp 514. The clamp 514 is then fastened to the angle iron assembly 510. In alternate embodiments, the bolt 514 can be fixedly coupled to the angle iron assembly 510 in any suitable manner. A torque applied to the top mounting assembly 504 can be measured at the bolt 514 as the shoot pack 200 rotates about its vertical axis. For example, a torque wrench can be used to measure the torque at the bolt 514 as the shoot pack 200 rotates. In alternate embodiments, any suitable torque measurement device can be used to measure the torque as the shoot pack 200 rotates. For example, in one embodiment, the torque measurement device can be embodied in or suitably coupled to the controller 300 shown in FIG. 1. In one embodiment, the test system 500 is configured to rotate the shoot pack 200 approximately 180 degrees, from about +90 degrees to about −90 degrees. This rotation is generally configured to mimic human torso loading and quantify the static torque required to rotate the shoot pack 200 to an extent of nearly 90 degrees.

In the example of FIG. 5, the test system 500 was configured to maintain an approximately 10 lb-f preload on the shoot pack 200. This allows the test system 500 to move the shoot pack 200 by rotating the shoot pack 200 at increasing angles. The combination of axial and torsional motion applied by the top mounting assembly 504 as the shoot pack 200 is rotated forces the shoot pack 200 to undergo bending in flexion and extension. In one embodiment, allowing one end of the system 500, either the top mounting assembly 504 or the bottom mounting assembly 506, to float at a preloaded value of tension, such as shown in the embodiment of FIG. 1, enables the generally simultaneous application of all three forces, axial, torsional and flexion/extension to the shoot pack 200 by the test system 500.

In one embodiment, chassis or frame 102 of the test system 100 illustrated in FIG. 1 is formed from a lightweight and strong extrusion material, such as aluminum. An extrusion such as aluminum can be easily assembled into unique, modular designs. In alternate embodiment, any suitable material can be used that provides the strength and resistance to bending as the test device 100 applies the axial, torsional and flexion/extension forces to the shoot pack 200.

Figure 6:
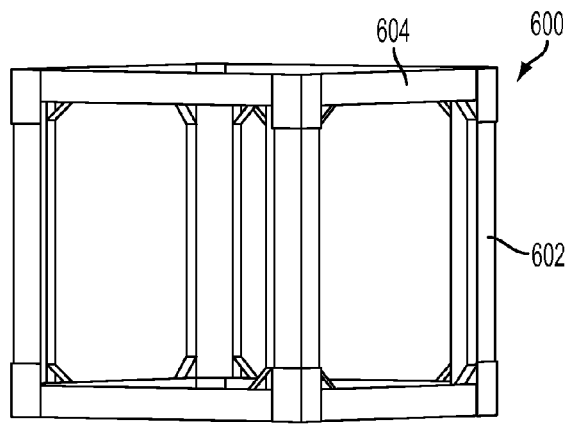
FIGS. 6-8 illustrates perspective views of aspects of a chassis for use in one embodiment of a soft body armor test system incorporating aspects of the present disclosure.
Figure 7:
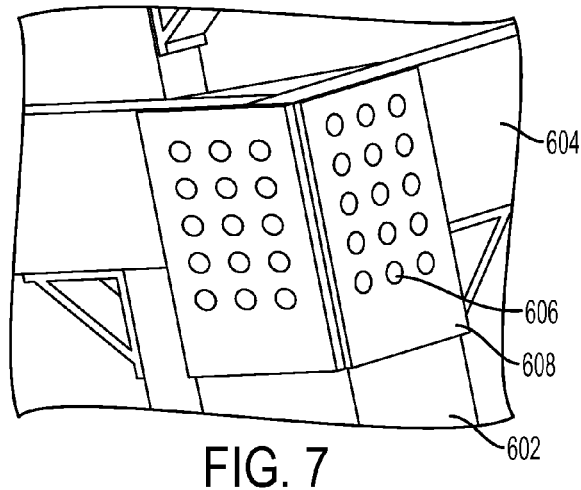
Figure 8:
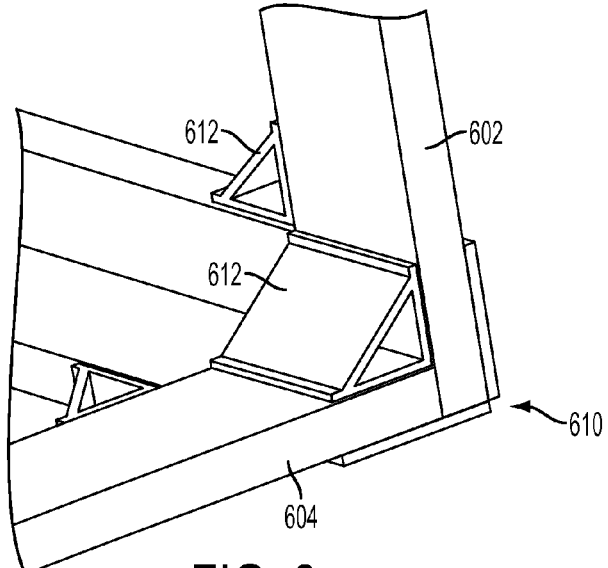

Referring to FIGS. 6-8, one embodiment of a chassis 600, similar to the chassis 102 of FIG. 1, is illustrated. In this example, the chassis 600 is a simple cube of aluminum extrusion. The extrusion members, generally illustrated as vertical members 602 and horizontal members 604, are joined together by joining plates 606, shown in FIG. 7. In this example, the joining plates 606 are approximately ¼ inch thick joining plates, although in alternate embodiments, any suitable sized joining plates can be used, other than including ¼ inch thick. Joining members 608, such as for example ⁵⁄₁₆ inch, number 18 screws, can be used to couple the joining members 608 to the extrusion members 602, 604. Alternatively, any suitable joining members can be used. In one embodiment, as is shown in FIG. 8, the corners 610 are reinforced with gussets 612 for added stiffness.

The soft body armor durability test system of the disclosed embodiments, such as the test system 100 shown in FIG. 1 is configured to impose cyclical work on the shoot pack by driving the shoot pack 200 in a clockwise direction approximately 90 degrees and a counter clockwise direction approximately 90 degrees, resulting in approximately 180 degrees of motion. A minimum static torque requirement of approximately 68 N-m (50 ft-lbs) was used to approach the 90 degree rotation. The requirements for the rotary actuator 110 shown in FIG. 1 to achieve these requirements are illustrated in Table 1. It will be understood that the specifications or requirements illustrated below are merely exemplary, and in alternate embodiments, the specifications of the rotary actuator 110 can be such as to impart the desired rotational forces on the shoot pack 200 in the test system 100.

TABLE 1

| Actuator requirements | | |
|---|---|---|
| Quantity | Value | Units |
| Static Torque | 67.8 | N-m |
| Oscillating Angle | 1.57 | Radians |
| Oscillating Time | 1.00 | Second |
| Moment of Inertia | 0.13 | Kg-cm$^2$ |
| Angular Acceleration | 1.57 | rad/s$^2$ |
| Acceleration Torque | 0.99 | N-m |
| Total Required Torque | 68.8 | N-m |
| Angular Velocity | 1.57 | rad/s |
| Inertial Energy | 0.16 | Joules |

In one embodiment, the rotary actuator 108 comprises a single shaft, 100 millimeter rotary bore actuator, with cushions and built-in magnets for switching capabilities. One example of such an actuator 108 is the SMC CDRA 1BS100-180C actuator, manufactured by SMC PNEUMATICS Tokyo, Japan. This particular type of actuator allows for 180 degrees of rotational motion.

In one embodiment, the solenoid valves 116 illustrated in FIG. 1 can comprise SMC VFS3000 series solenoid valves coupled to a NVFS3000 series manifold block manufactured by SMC PNEUMATICS Tokyo, Japan. The minimum and maximum operating pressures were 22 psi and 150 psi, respectively. The power consumption of the exemplary solenoid noted above is approximately 1.8 watts at 12 volts-DC. In alternate embodiments, any suitable solenoid/manifold 116 can be used, other than the example above.

To control the position of the shoot pack 200 during actuator motion as described above, two linear pillow-block bearings 112 were used, one at each end of the bottom mounting assembly 106 as is shown in FIG. 1. The pillow-block bearings 112 are attached to the bottom mounting assembly 106 and control the vertical motion of the shoot pack 200 along the bearing rods 108. One example of a pillow-block bearing is a Thomson SPB-16 bearing, manufactured by THOMSON, Radford, Va.

In one embodiment, a control system or controller 300 can be coupled to the solenoid valves 116 and actuator 110 to control the soft body armor test system 100 as is generally described herein. The controller 300 shown in FIG. 1 can be any suitable device that is configured to operate the soft body armor durability test device 100 as is generally described herein. For example, in one embodiment, the controller 300 comprises one or more of processors and microprocessors that are configured to execute computer readable instructions in order to carry out the test processes described herein. For example, the controller 300 can comprise a computing device with a memory for storing data, computer readable program code and instructions, such as software, as is generally understood. The controller 300 can interfaced with, and coupled to the soft armor test system 100 in any suitable manner, including wired and wireless connections.

Figure 9:
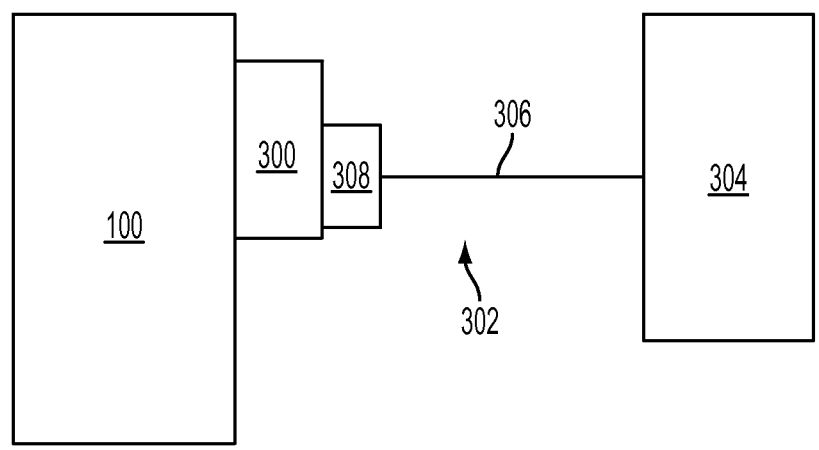
FIG. 9 illustrates a block diagram of one embodiment of a control system for a soft body armor test system incorporating aspects of the present disclosure.

Referring to FIG. 9 for example, in one embodiment, the controller 300 includes or is coupled to an interface 302 to connect the system 100 to a computer 304, such as a laptop computer for example, as is generally illustrated in FIG. 9. Although the controller 300 and interface 302 are shown as separate components, in alternate embodiments, the controller and the interface 302 can be integrated in either of the controller 300 or computer 304, depending upon the application. In one embodiment, the controller 300 could be part of or comprise the computer 304.

In one embodiment, the interface 302 comprises an RS232 relay or relay board 308 coupled to the computer 304 via a serial to USB cable 306 as is shown in FIG. 9. In alternate embodiments, the interface 302 can comprise any suitable communication or control interface to coupled the computer 304 to the system 100. For this example, terminals on the RS232 relay 308 are electrically coupled to the solenoid(s) 116 to power them ON/OFF based on input from the computer 304. The relay board 308 receives signals from the computer 304 to actuate the solenoid valves 116 that supply air to the actuator 110. In this example, the relay control board 308 is powered by a 12 volt-DC power supply and the relays themselves are capable of power consumption up to 10 amps at 24 volts-DC. In one embodiment, the interface 302 can be embodied in computer readable instructions stored in the memory of the computer 304.

Figure 10:
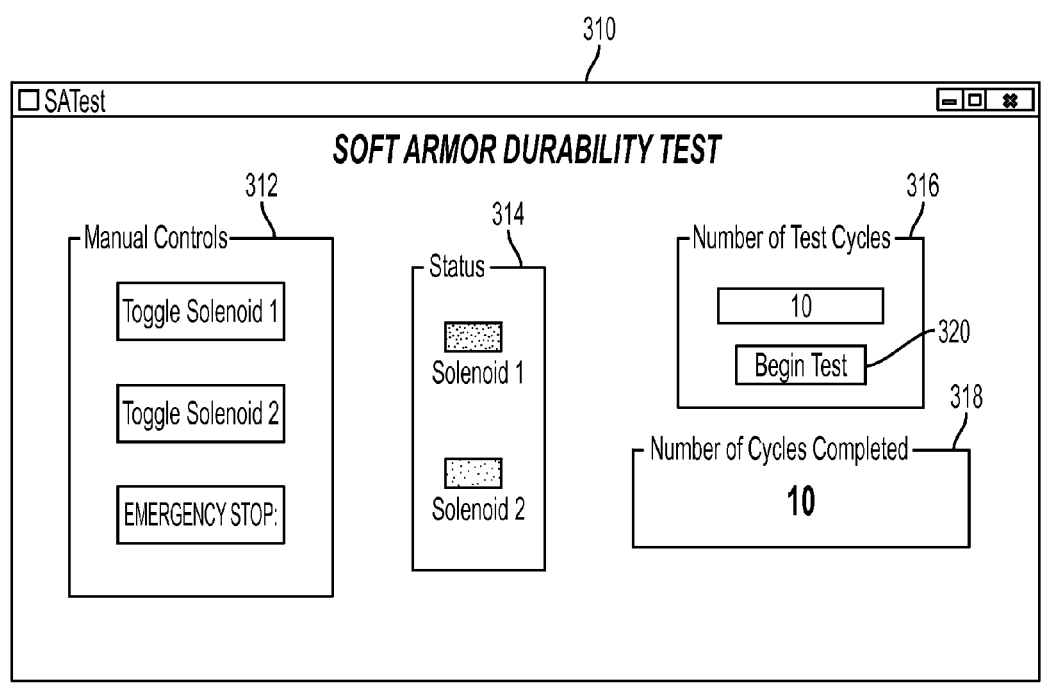
FIG. 10 illustrates a screen shot of one embodiment of a graphical user interface for one embodiment of a soft body armor test system incorporating aspects of the present disclosure.

One example of an exemplary graphical user interface 310 for the soft armor test system 100 of the disclosed embodiments is shown in FIG. 10. In one embodiment, options for manual firing of the solenoids 116 include buttons 312. The cyclical firing of the solenoids 116 can also be based on a timer object. Status lights 314 can indicate the position of each solenoid 116. For example, a green light can indicate an open solenoid, while a red light can indicate a closed solenoid. In alternate embodiments, any suitable indicators can be used to indicate the open and closed positions of the solenoids 116. The number of test cycles can be set in an option box or control 316. The number of completed test cycles can be indicated in an indicator box 318. It will be understood that the graphical user interface 310 shown in FIG. 10 is merely exemplary and can be embodied in many different forms and options, the scope of which is contemplated by the disclosure contained herein.

Figure 11:
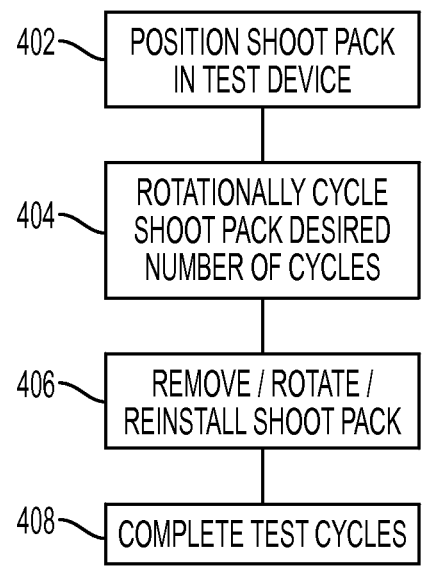
FIG. 11 illustrates one embodiment of a process for durability testing of a ballistic shoot pack using a soft body armor test system incorporating aspects of the present disclosure.

FIG. 11 illustrates an exemplary process for carrying out a soft body armor durability test using the soft body armor test system 100 of the disclosed embodiments. The process described herein is merely exemplary and it will be understood that the process described herein can be embodied in different forms, the scope of which is contemplated herein.

In one embodiment, the shoot pack 200, also referred to as a test sample, is conditioned at 68±10 degree Fahrenheit for at least 24 hours prior to testing. The testing is performed in a standard atmosphere of 68±10 degree Fahrenheit and 50±20% relatively humidity. Temperature and humidity measurements can be recorded before the beginning of each test. The following is the procedure for conditioning a shoot pack 200 using this durability apparatus:

Make sure air supply is off, communications between laptop 304 and device 100 are disabled, and actuator 108 moves freely.

Place 402 shoot pack 200 into the device 100 and center in between the top and bottom clamping assemblies 104, 106.

Tighten clamping assemblies 104, 106 sufficiently such that the shoot pack 200 will not pull out during cycling (with a torque up to approximately 50 ft-lbs).

The shoot pack 200 is installed while the actuator 110 is in the middle of travel.

The shoot pack 200 should generally be disposed parallel to the clamping assemblies that hold the shoot pack 200 in the device 100.

Turn on air supply at regulator 118 (regulate to approximately 90 psig depending on desired torque value).

Open the desired COM port on the GUI 310.

Enter the desired number of cycles (typically this is the total cycles/2) in the GUI 310.

Click 'Begin Test' 320. The shoot pack 200 will be rotationally cycled 404.

Once the desired number of cycles are complete, remove the shoot pack 200, rotate the shoot pack 200 90 degrees and reinstall 406 the shoot pack 200 between the top and bottom mounting assemblies 104, 106.

Re-tighten the top and bottom mounting assemblies 104, 106 to fixedly couple the shoot pack 200 and complete 408 the rest of the test cycles.

In one embodiment, the method described herein includes conditioning the shoot pack 200 in the test device 100 as is generally described herein. The conditioned shoot pack 200 is then ballistically tested in a manner as is generally understood.

The aspects of the disclosed embodiments provide a soft body armor testing system and device that is capable of mechanically inducing a flexible armor sample, at a system level, to a combination of axial, torsional and bending (flexion/extension) forces substantially simultaneously. The soft body armor testing system of the disclosed embodiments induces these forces in a single loading condition and substantially replicates actual body armor displacements when worn and the human ability to impart stress on the armor system.

Thus, while there have been shown, described and pointed out, fundamental novel features of the invention as applied to the exemplary embodiments thereof, it will be understood that various omissions and substitutions and changes in the form and details of devices and methods illustrated, and in their operation, may be made by those skilled in the art without departing from the spirit of the invention. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An assembly for testing a durability of a soft body armor system, comprising:
    a top mounting assembly;
    a bottom mounting assembly, the soft body armor system being fixedly disposed between the top mounting assembly and the bottom mounting assembly;
    a rotary actuator coupled to the top mounting assembly, the rotary actuator configured to rotate the top mounting assembly in a range of approximately +90 degrees to and including −90 degrees;
    a linear bearing on each end of the bottom mounting assembly; and
    a bearing rod on which each linear bearing is configured to ride
    wherein a weight of the bottom mount assembly preloads the soft body armor system in tension.

2. The assembly of claim 1, wherein a rotation of the top mounting assembly induces a torsional force on the soft body armor system.

3. The assembly of claim 1, wherein a rotation of the top mounting assembly induces torsional, axial and bending forces substantially simultaneously on the soft body armor system.

4. The assembly of claim 1, wherein a rotation of the top mounting assembly induces a substantially vertical motion of the bottom mounting assembly along the bearing rods.

5. The assembly of claim 1, comprising a shaft coupler coupling the top mounting assembly to the rotary actuator.

6. The assembly of claim 1, wherein the top mounting assembly comprises a clamp to removably secure a top portion of the soft body armor system to the top mounting assembly.

7. The assembly of claim 1, wherein the bottom mounting assembly comprises a clamp to removably secure a bottom portion of the soft body armor system to the bottom mounting assembly.

8. The assembly of claim 1, wherein the soft body armor system comprises a ballistic shoot pack.

9. The assembly of claim 1, wherein the bottom mounting assembly is in a fixed non-rotational position relative to a vertical axis while the top mounting assembly rotates about the vertical axis.

10. A method for durability testing of a soft body armor system, comprising: positioning a ballistic shoot pack between a top mount assembly and a bottom mount assembly, the top mount assembly being configured to rotate about a vertical axis; rotating the top mount assembly to apply a torsional force to the ballistic shoot pack, the bottom mount assembly remaining stationary about the vertical axis.

11. The method of claim 10, wherein rotation of the top mount assembly induces torsional, axial and bending forces substantially simultaneously on the ballistic shoot pack.

12. The method of claim 10, wherein the bottom mount assembly is configured to move upwards in a vertical direction as the top mount assembly rotates.

13. The method of claim 12, wherein the upward movement of the bottom mount assembly induces compressive stresses on the ballistic shoot pack.

14. The method of claim 10, wherein the top mount assembly is configured to rotate in a range of approximately +90 degrees to and including −90 degrees.

15. The method of claim 10, wherein the ballistic shoot pack is a soft body armor system.

16. The method of claim 10, wherein the ballistic shoot pack is preloaded in tension by a weight of the bottom mount assembly.

17. A shoot pack test assembly, comprising:
    a chassis;
    a set of bearing rods fixedly attached to the chassis;
    a bottom mount assembly having a first end and a second end;
    a linear bearing coupled to the first end and the second end of the bottom mount assembly and configured to ride on a respective bearing rod;
    a rotary actuator coupled to the chassis;
    a top mount assembly coupled to the rotary actuator, the rotary actuator configured to rotate the top mount assembly in a range of between approximately +90 degrees to and including −90 degrees about a vertical axis between the bottom mount assembly and the top mount assembly; and
    a shoot pack disposed between the bottom mount assembly and the top mount assembly;
    wherein the rotation of the top mounting assembly by the rotary actuator induces torsional, axial and bending forces substantially simultaneously on the shoot pack; and
    wherein a weight of the bottom mount assembly preloads the shoot pack in tension between the top mount assembly and the bottom mount assembly and the rotation of the top mount assembly by the rotational actuator induces an upward movement of the bottom mount assembly along the bearing rods to induce compressive stresses on the shoot pack.

* * * * *